United States Patent
Layus et al.

(10) Patent No.: US 11,213,554 B2
(45) Date of Patent: Jan. 4, 2022

(54) COMPOSITION FOR IMPROVING THE HEALTH OF LIVESTOCK

(71) Applicant: NOLIVADE, Changé (FR)

(72) Inventors: Michel Layus, Pleumeur Bodou (FR); Alexandre Brame, Rennes (FR)

(73) Assignee: NOLIVADE, Changé (FR)

( * ) Notice: Subject to any disclaimer, the term of this patent is extended or adjusted under 35 U.S.C. 154(b) by 0 days.

(21) Appl. No.: 16/762,278

(22) PCT Filed: Nov. 8, 2018

(86) PCT No.: PCT/EP2018/080670
§ 371 (c)(1),
(2) Date: May 7, 2020

(87) PCT Pub. No.: WO2019/092136
PCT Pub. Date: May 16, 2019

(65) Prior Publication Data
US 2020/0353019 A1    Nov. 12, 2020

(30) Foreign Application Priority Data

Nov. 8, 2017    (FR) ...................................... 1760496

(51) Int. Cl.
*A61K 35/744*   (2015.01)
*A61P 31/04*   (2006.01)
*A61K 9/06*   (2006.01)

(52) U.S. Cl.
CPC .............. *A61K 35/744* (2013.01); *A61K 9/06* (2013.01); *A61P 31/04* (2018.01)

(58) Field of Classification Search
None
See application file for complete search history.

(56) References Cited

U.S. PATENT DOCUMENTS

2020/0353019 A1* 11/2020 Layus .................. A61K 35/744

FOREIGN PATENT DOCUMENTS

| RU | 2 546 880 C2 | 4/2015 |
| RU | 2 612 009 C1 | 3/2017 |
| WO | 2013/178947 A1 | 12/2013 |
| WO | 2014/151837 A1 | 9/2014 |

OTHER PUBLICATIONS

International Search Report dated Feb. 13, 2019 in corresponding International Application No. PCT/EP2018/080670; 6 pages.
Database WPI, Week 201543, Thomson Scientific, London, BG; AN 2015-241592 XP002783772; 2 pages.
Maneewan, C. et al., "Development of Bacillus subtilis MP and effective utilization on productivity and microorganisms in feces of suckling piglets", International Journal of Applied Research in Veterinary Medicine, Veterinary Solutions, US, vol. 9, No. 4, Jan. 1, 2011, pp. 382-387.
Lee, D. J. et al., "Evaluation of probiotic treatment in a neonatal animal model", Pediatric Surgery International 2000, vol. 16, No. 4, 2000, pp. 237-242.

* cited by examiner

*Primary Examiner* — Padmavathi Baskar
(74) *Attorney, Agent, or Firm* — Maier & Maier, PLLC

(57) ABSTRACT

A method for the prevention or treatment of infections contracted by newborns of livestock mammals, which includes applying a composition that includes a mixture of bacterial strains to the perineum and/or the teat(s) of female livestock mammal that is going to give birth or has given birth to the newborn livestock mammals. Also, a kit for preventing digestive, respiratory or other infections in newborn livestock mammals, which includes at least one composition and at least one application element for applying the composition to the perineum and/or to the teats of the female livestock mammals.

10 Claims, 1 Drawing Sheet

COMPOSITION FOR IMPROVING THE HEALTH OF LIVESTOCK

FIELD

The invention relates to a composition for improving the health of livestock, in particular livestock mammals.

BACKGROUND

Mammals are born having a sterile digestive tract. The appearance of intestinal flora therefore substantially depends on the environment and the particular physiological features of each species. In these conditions, the colostrum ingested during the first days of life will in principle protect the newborn against digestive infections. This protection is possible only if the maternal colostrum is itself qualitatively and quantitatively adapted and suitable.

The mammalian immune protection has, as its starting point, an intestinal immunity process which inevitably has an impact on the implementation of said immunity. This results in the possible emergence of neonatal infections in young mammals, from the 24th or 48th hour of life, due to insufficient protection, and this may last until the 21st day, which is the date when local immunity emerges.

The animal food industry is considered, more and more, to have a role to play in ensuring responsible use of food antimicrobials in animal production. The decision-makers are asking animal food producers, farmers, vets and regulatory authorities to work together to determine the best practices for breeding and hygiene, and viable alternatives, in order to reduce the use of antibiotics in livestock and to improve the wellbeing of the animals.

In order to respond to the new demands of modern agriculture, and taking account of the biological constraints of mammals, it is necessary to develop a method for protecting the breeding environment and the intestinal flora of newborns.

The prior art proposes applications to the teats of females, with the aim of treating mastitis, for example in the application RU2612009. However, these methods aim to treat the teats of the females, but do not aim to improve the health of the newborns.

In turn, other methods known from the prior art aim to treat the breeding environment of the newborns, in order to promote their growth and their wellbeing.

Despite these attempts, the need remains to propose an improvement in conditions favorable for the good development of newborns.

The invention aims to resolve this lack.

SUMMARY

One object of the invention is that of proposing a method for preventing health risks and for improving the breeding performance of mammals, as well as a microbial composition.

Thus, the invention relates to a composition comprising or substantially consisting of a mixture:
1. of at least one strain of bacteria of the genus *Bacillus*, in particular a *Bacillus subtilis* strain, and
2. of at least one strain of lactic bacteria, for the use thereof within the context of prevention or treatment of infections contracted by a newborn livestock mammal at the time of birth, in particular digestive or respiratory infections, said composition being applied to the perineum and/or to the teats of the female that is going to give birth or has given birth to said newborn livestock mammals, the application being carried out before and/or after parturition.

DETAILED DESCRIPTION

Figure 1:
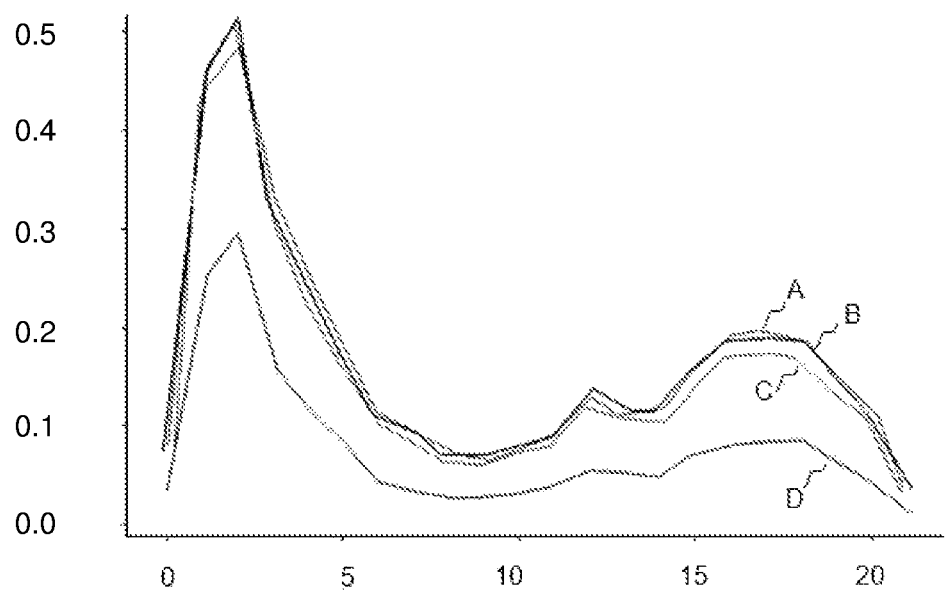
FIG. 1 is a graph showing the probability of occurrence of diarrhea in piglets in a box, as a function of time (in days) after birth (t=0), in batches 1 to 3 (curves A to C) treated with an antibiotic, and batch 4, treated only with the composition according to the invention (curve D).

The invention is based on the surprising finding, made by the inventors, that the combined use of at least one strain of lactic bacteria and at least one *Bacillus* strain, when applied, before or after parturition, to the perineum and/or the teats of females, makes it possible to protect the newborns, from a very young age (from parturition), against infections harmful to their development, and thus to promote and improve their growth.

A composition as used in the invention is advantageous in that it acts internally in the animal and in its external environment, making it possible to create a flora barrier from a very young age.

In the invention, "teats and/or perineum" is intended to mean that the application takes place either on the perineum alone, or on one or more teats alone, or by way of combining applications on the perineum and on at least one teat, or even all the teats.

Advantageously, in the invention, application to the perineum can cover either application to the perineum alone, or intra-vaginal application, or both application to the perineum and intra-vaginal application.

Advantageously, in the invention, application to the teat(s) corresponds to external application carried out on the teats of the female mammals, but can also correspond to intra-mammary application to said teats of said female mammals.

The intra-mammary application is achieved for example by means of syringes introduced into the gland duct of the teats of said female mammals. A person skilled in the art knows the most appropriate techniques for performing intra-mammary applications of this kind.

In the invention, it is important for the female giving birth to the newborn to be treated to be the one receiving the application of the above-mentioned composition. Indeed, what is important is that the newborn should be in contact with the treated perineum as soon as it leaves the uterus of the female, and/or that its first suckling should be from a treated teat.

"At least one bacteria strain of the genus *Bacillus*" means that one strain, or two strains, or three strains, or more, of *Bacillus* can be used in the context of the invention. In the same way, "at least one strain of lactic bacteria" means that one strain, or two strains, or three strains, or more, can be used in the composition defined above.

In the invention, a strain of bacteria is intended to mean all the individuals (bacteria) resulting from successive transplanting of a bacterial colony.

In other words, a strain is a part of a bacterial species that differs from the other bacteria of the same species by a minor but identifiable difference. A strain is also defined as a population of bacteria that originates from one single organism or the pure isolate culture. The strains of the same species may differ slightly from one another in many respects.

The application to the perineum and/or to the teat(s) is carried out in conditions in which all or almost all of the treated parts are covered by the composition according to the invention. Indeed, it is not essentially necessary for the treated part to be completely covered, but what is essential is that the quantity of the composition should be sufficient for the newborn to be in contact with sufficient bacteria to protect it against infections.

Since the application of the composition according to the invention is carried out before and/or after the parturition, this means that the composition is applied to the perineum before, after, or before and after, the parturition, the composition is applied to the teat(s) before, after, or before and after, the parturition, or the composition is applied to the perineum and to the teat(s) before, after, or before and after, the parturition.

The teat and/or perineum applications can be carried out simultaneously, separately, or in a manner spread over time.

Advantageously, the invention relates to the composition for the above-mentioned use, wherein the bacterial composition comprises:

at least one of the following three *Bacillus subtilis* strains: NOL01, NOL02, NOL03, said strains being deposited in the CNCM under the numbers: CNCM I-4606, CNCM I-5043 and CNCM I-4607, respectively, and at least the lactic bacteria strain: *Lactococcus lactis* spp *lactis* 1 strain NOL11, said strain being deposited in the CNCM under number CNCM I-4609.

The invention relates to the use of at least one strain, selected from the strains NOL01, NOL02 and NOL03, and at least the strain NOL11. Thus, the invention covers the 7 following combinations:

NOL01 and NOL11,
NOL02 and NOL11,
NOL03 and NOL11,
NOL01, NOL02 and NOL11,
NOL01, NOL03 and NOL11,
NOL02, NOL03 and NOL11, and
NOL01, NOL02, NOL03 and NOL11.

All said strains were deposited in the National Collection of Cultures of Microorganisms (CNCM) at the Pasteur Institute in Paris, in accordance with the Budapest Treaty.

More advantageously, the invention relates to a composition for the above-mentioned use thereof, said composition comprising $10^4$ to $10^{11}$ bacterial colonies of *Bacillus* and $10^4$ to $10^{11}$ bacterial colonies of lactic bacteria, the bacterial colonies being per ml or g of composition.

In other words, in this advantageous embodiment, if the composition according to the invention is in liquid form, said composition will comprise $10^4$ to $10^{11}$ bacterial colonies of *Bacillus* per ml of composition, and $10^4$ to $10^{11}$ bacterial colonies of lactic bacteria per ml of composition.

If, in contrast, the composition is in a non-aqueous form, or even dehydrated, said composition will comprise $10^4$ to $10^{11}$ bacterial colonies of *Bacillus* per g of composition, and $10^4$ to $10^{11}$ bacterial colonies of lactic bacteria per g of composition.

In the invention, $10^4$ to $10^{11}$ bacterial colonies means: approximately $10^4$, approximately $5 \cdot 10^4$, approximately $10^5$, approximately $5 \cdot 10^5$, approximately $10^6$, approximately $5 \cdot 10^6$, approximately $10^7$, approximately $5 \cdot 10^7$, approximately $10^8$, approximately $5 \cdot 10^8$, approximately $10^9$, approximately $5 \cdot 10^9$, approximately $10^{10}$, approximately $5 \cdot 10^{10}$ or approximately $10^{11}$ bacterial colonies.

A particular application for the female mammal is from $10^5$ to $10^{11}$ bacterial colonies per female, for each application. That is to say that each bacterium is present at an amount of $10^5$ to $10^{11}$ bacterial colonies per female for perineum application, and $10^5$ to $10^{11}$ bacterial colonies per female for teat application.

A person skilled in the art easily knows how to determine said number of bacteria, in particular by counting either manually (using a Malassez blade), or by using an automatic cell counter, or by dilution and then seeding on agar-agar and counting the colonies.

Even more advantageously, the invention relates to the use as defined above, wherein said at least one *Bacillus* strain is in sporulated and/or vegetative form.

The lactic bacteria are, in turn, always in vegetative form. Thus, the composition according to the invention comprises at least one *Bacillus* strain in sporulated form, and at least one strain of lactic bacteria in vegetative form, or comprises at one *Bacillus* strain in vegetative form and at least one strain of lactic bacteria in vegetative form.

Advantageously, the invention relates to a composition for the use thereof as defined above, said composition being applied to the perineum and/or to the teats of the female that is going to give birth or has given birth to said newborn livestock mammals, the application being carried out before and/or after parturition, said female being in an environment previously treated with said composition.

In the invention, it is advantageous that, prior to the application on the teat(s) and/or the perineum of the females, the breeding environment of said females should be treated with the composition according to the invention, before said females are introduced into said environment, or even on the day of their arrival.

Application in the environment makes it possible to control and/or position the bacterial flora of the environment of the females, while reducing the pathogenic pressure. This can be achieved by nebulization or spraying the breeding buildings, including the litter . . . . Less contamination of the animals is observed, since there are fewer pathogenic outbreaks. An application of this kind gambles on the living or surviving pathogens in the environment. The methods for spreading in the environment are spraying, nebulization, covering surfaces with foams, or even powdering using composition powder according to the invention.

Advantageously, the invention relates to the composition for the above-mentioned use, said composition substantially consisting of:

the following three *Bacillus subtilis* strains: NOL01, NOL02, NOL03, said strains being deposited in the CNCM under the numbers: CNCM I-4606, CNCM I-5043 and CNCM I-4607, respectively, and the lactic bacteria strain: *Lactococcus lactis* spp *lactis* 1 strain NOL11, said strain being deposited in the CNCM under number CNCM I-4609.

It is particularly advantageous for the composition to comprise the three *Bacillus subtilis* bacterial strains mentioned above, in vegetative or sporulated form, and the above-mentioned lactic bacteria strain, in vegetative form.

Even more advantageously, the invention relates to the above-mentioned composition, for the above-mentioned application thereof, where said infections are intestinal infections, in particular neonatal diarrhea, enteritis, *salmonella*, respiratory infections, and in particular rhinitis, pasteurellosis, bordetellose, cutaneous infections, and in particular ulcers, epidermitis, necroses and infections in the locomotive system, in particular infectious lameness, in particular the various forms of arthritis.

Indeed, as shown in the examples below, the flora made up by the composition according to the invention will be ingested by the newborns and will make it possible to control and/or position the flora present in the digestive and/or respiratory systems, reducing the existing or arising pathogenic pressure (since the digestive and respiratory systems are possible entry paths for pathogens responsible for pathologies associated with other systems of the organism). Another effect will be the stimulation of the animals' natural defenses. The flora also acts directly on the digestive health of the animals, and limits the entry of other pathogens, which is advantageous when the newborn has not acquired its definitive immunity.

Advantageously, the invention relates to the above-mentioned use, where said composition is applied to the perineum and/or the teat(s) by spraying, spreading, powdering or soaking.

Depending on the application method used, a person skilled in the art will select the most appropriate material, and in particular will prefer a liquid composition for spraying or soaking, and will favor a dehydrated composition for application by means of powdering.

Furthermore, a method is provided for preventing or treating infections contracted by newborn livestock mammals at the time of birth, in particular digestive infections, the method comprising a step of application to the perineum and/or to the teats of the female that is going to give birth or has given birth to said newborn livestock mammals, the application being carried out before and/or after parturition, an effective dose of a composition comprising, or substantially consisting of, a mixture:
1. of at least one strain of bacteria of the genus *Bacillus*, in particular a *Bacillus subtilis* strain, and
2. of at least one strain of lactic bacteria.

In particular, a method is provided as defined above, where said composition comprises
   at least one of the following three *Bacillus subtilis* strains: NOL01, NOL02, NOL03, said strains being deposited in the CNCM under the numbers: CNCM I-4606, CNCM I-5043 and CNCM I-4607, respectively, and
   at least the lactic bacteria strain: *Lactococcus lactis* spp *lactis* 1 strain NOL11, said strain being deposited in the CNCM under number CNCM I-4609, and in particular where said composition comprises
   the following three *Bacillus subtilis* strains: NOL01, NOL02, NOL03, said strains being deposited in the CNCM under the numbers: CNCM I-4606, CNCM I-5043 and CNCM I-4607, respectively, and
   the lactic bacteria strain: *Lactococcus lactis* spp *lactis* 1 strain NOL11, said strain being deposited in the CNCM under number CNCM I-4609.

In the method described above, the quantities of bacteria mentioned above are applicable.

The invention furthermore relates to a kit for preventing digestive, respiratory or other infections in newborn livestock mammals, substantially comprising:

at least one composition as defined above, and
at least one application means for applying said composition to the perineum and/or to the teats of the female that is going to give birth or has given birth to said newborn livestock mammals.

The kit according to the invention may consist of a predefined mixture of bacteria as defined above, or a plurality of separate bottles of sachets comprising one or more bacterial strains according to the invention.

The application means contained in the above-mentioned kit can be brushes for application by spreading, cartridges to be used for spraying, an atomizer, a soaking tool, or any other means allowing for application as defined above, in particular spraying, spreading, powdering or soaking.

The invention will be better understood and illustrated upon reading the following examples and figures.

EXAMPLES

Example 1

The aim of this test is to reduce the use of antibiotics in livestock. This desire is accompanied by a significant increase in the development of all the alternative solutions: vaccination, breeding practice, biosecurity and substitution products, etc. Acting on the bacterial ecosystems that interact with the animal is therefore a promising pathway, and using barrier flora is part of this approach.

This test shows the results obtained by a breeder who already uses barrier flora in peri-parturition, and who wished to reevaluate their protocol (a new formulation of the barrier flora (NOL01, NOL02, NOL03, NOL 11) as well as lightened application rhythm).

Material and Methods

The livestock followed is 700 breeding, fattened sows selected for breeding (5 groups of 120 sows). The test was carried out on 2 groups, each made up of 3 batches of 40, adhering to a homogeneous distribution of the ranges of scope. The application protocol comprises spraying the composition according to the invention in the environment, on the teats and the perineum of the sows, as well as probiotic administration to the sows via the mashing machine.

Table 1 summarizes the spraying protocols applied. All the sows received a dose of probiotics in the trough, from day-3 to day 1, with respect to the parturition.

TABLE 1

Protocols of spraying the flora

|  | Batch 1 - control | Batch 2 - control | Batch 3 - control | Batch 4 - test |
|---|---|---|---|---|
| Application rhythm | Former | Former | New, lighter | New, lighter |
| Formula | Former | New | New | New |
| Group | 1 + 2 | 1 | 1 + 2 | 2 |
| Antibiotics on piglets | yes | yes | yes | no |
| Day-3 Day-2 | Environment | Environment | Environment | Environment |
| Day-1 | Teats and perineum | Teats and perineum | Teats and perineum | Teats and perineum |
| Day 0: Parturition |  |  |  |  |
| Day 1 | Teats and perineum | Teats and perineum | Teats and perineum | Teats and perineum |

TABLE 1-continued

Protocols of spraying the flora

| | Batch 1 - control | Batch 2 - control | Batch 3 - control | Batch 4 - test |
|---|---|---|---|---|
| Day 4 | Teats and perineum | Teats and perineum | | |

For batches 1 to 3, the breeder administered an antibiotic injection to the piglets at the time of treatment; they are therefore control batches. The breeder agreed to stop this administration for some of the piglets, corresponding to batch 4; this is therefore the test batch. Indeed, the antibiotic has an effect on the composition according to the invention, and thus cancels out the potential effect thereof. Batches 1 to 3 thus represent positive control batches (treated with antibiotics), and batch 4, the test, represents an application on the teats and the perineum. Then, daily recordings were taken on the following features:

Grading of the feces: 0 normal, 1 soft (deteriorated), 2 dung-like, 3 liquid,

Cleanliness of the piglets: 0<20% soiled, 1 between 20 and 50% soiled, 2 more than 50% soiled mortality and causes treatments and motives.

The statistical analyses were carried out on the R software (free access reference software; R Development Core Team (2008). R: A language and environment for statistical computing. R Foundation for Statistical Computing, Vienna, Austria). The model used is the logistical model.

Results

1) Diarrhea in the Piglets

First of all, just after birth, the occurrence of diarrhea in at least one piglet per box is evaluated. The results are shown in FIG. 1.

The statistical modelling shows that the risk of occurrence of diarrhea in the newborn, in one box, is thus significantly reduced in piglets that have been in the presence of the composition according to the invention, applied to the perineum and the teats of their mother, compared with the same piglets treated with an antibiotic.

This risk is reduced by 50% in this case.

It will be noted that, within the context of batch 4, the breeder carried out 30% fewer medical treatments in order to care for the animals.

2) Mortality of the Piglets

Different causes of mortality were identified: killed "small" (around 7% of the piglets), mortality due to digestive reasons (approximately 2%), mortality due to crushing (approximately 2%), and other causes (approximately 4%).

Figure 2:
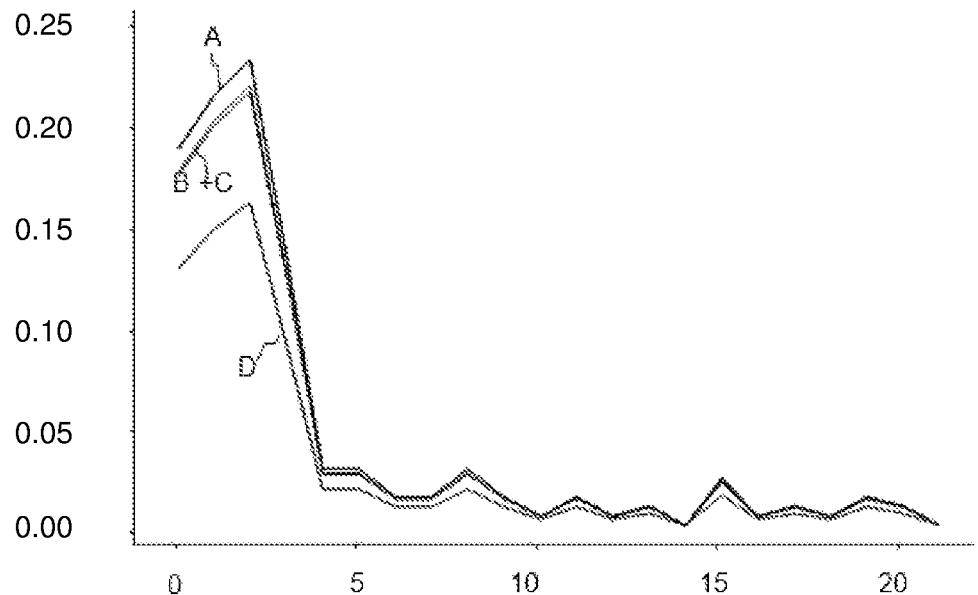
FIG. 2 is a graph showing the probability of death (excluding the mortality of the "small" ones killed) of piglets in a box, as a function of time (in days) after birth (t=0), in batches 1 to 3 (curves A to C) treated with an antibiotic, and batch 4, treated only with the composition according to the invention (curve D).

In order to analyzes the results, the inventors did not keep the "small, killed" cause, since it was not influenced by the application of the composition according to the invention in peri-parturition. The modelling shows the risk of mortality of all other causes together, at the scale of one box (FIG. 2).

The development of the risk of mortality in batch 4 is significantly different from the 3 other batches (p-value=0.067).

DISCUSSION

This study reveals an equivalence in the results between the two formulations and rhythms of application of the barrier flora.

Significant positive differences were demonstrated, using the protocol without antibiotic injection of the piglets, on the occurrence of diarrhea and the overall mortality. This improvement is associated with the lack of possible inhibition of the flora, by the antibiotic.

CONCLUSION

The observations made on the batch without antibiotic clearly show the effectiveness of the composition according to the invention on the health of the piglets (less diarrhea and mortality) when the piglet is in contact with the composition according to the invention, directly after its birth.

Example 2

This test aims to confirm the significance of application of flora (NOL01, NOL02, NOL03, NOL 11), during maternity, directly on the teats and perineum of the sows, with the aim of improving the health of the piglets, and in particular of reducing neonatal diarrhea.

1. Protocol

The test took place in a common pig maternity unit, on 2 consecutive groups, with a control room and a test room for each group, with approximately 18 spaces in each. The test was carried out upon the sows entering maternity, and until the piglets were weaned at 21 days.

1. Planning the Test and Applications:

Prior to launching the test, a 2-day cleaning/disinfection cycle was carried out in all the rooms, control and test, prior to the arrival of the sows into the maternity unit.

Upon arrival of the sows in the maternity unit on day-3, day 0 being the day of the first parturition, the breeding environment, i.e. all the walls, floors and materials (partitions, feeders, etc.) of the test rooms were treated by means of spraying the solution according to the invention (NOL01, NOL02, NOL03, NOL11).

From day-1, the solution according to the invention, as prepared according to protocol b—below, was applied by means of spraying, onto the teats and perineum of the test sows. This double application, to the teats and perineum, was then repeated daily, until the parturition.

Following parturition, only the teat application was repeated every day, until day 5, in the test rooms.

During the first days of its life, until weaning, the piglet feeds exclusively on maternal milk (no other food, either liquid or solid). The piglet will thus regularly suck the teats of its mother. Thus, applying the solution according to the invention to the teats of the mothers allows for the flora to be ingested by the piglets.

Following parturition, the piglets, and the state of the boxes, were monitored until weaning, i.e. 3 weeks (21 days).

1. Implementation of the Solution According to the Invention:

A dose of the solution according to the invention is packaged in two separate bottles, of 20 ml each:

A bottle B containing the *Bacillus* (NOL01, NOL02 and NOL03)

A bottle L containing the *Lactococcus* (NOL11)

The bottles are brought to the breeding area frozen.

Preparation of a Stock Solution:

A stock solution was prepared following defrosting of a dose of the solution according to the invention (1 bottle B and 1 bottle L) for 1 hour at ambient temperature, or 5 minutes in cold water. This defrosted dose was added to 310 ml of untreated drinking water, in a measuring can, which was subjected to homogenization by means of agitation. The stock solution thus prepared was kept in the refrigerator until the applications had finished (day 5).

Preparation for Spraying:

Each day of the test (from day-1 to day 5), 50 ml of the stock solution was removed and poured into the tank of a sprayer that had not contained any disinfectant, and then 500 ml of untreated drinking water was added. This new preparation was then sprayed onto the teats and the perineum of the sows of the test rooms, according to the protocol a—described above.

1. Measurements

The following zootechnic parameters were collected throughout the duration of the maternity, until weaning of the piglets at 21 days, in each of the test and control boxes:

Growth: individual weight of the piglets (collected weekly throughout the maternity period, i.e. 3 times);
Diarrhea: number of boxes with occurrence of diarrhea, and estimated proportion of piglets affected per box;
Digestive mortality: number of piglets that died, per box, due to a digestive pathology;
Antibiotics: number of antibiotic treatments applied per box, and type of treatment.

1. Results

An a posteriori check of the division into batches was carried out by analyzing the birth weight of the piglets, the number of piglets per sow and per batch, the date of parturition, and the range of the scope.

TABLE 2

|  | Group 1 | | Group 2 | |
| --- | --- | --- | --- | --- |
| Batch | Test | Control | Test | Control |
| Diarrhea (% of number of boxes affected) | 60%$^a$ | 85%$^b$ | 85% | 85% |
| Antibiotic treatments (number per box) | 0.6$^a$ | 2.4$^b$ | 1.9$^a$ | 3.3$^b$ |
| Digestive mortality (number of deaths per box) | 0.5 | 0.8 | 0.7$^a$ | 2.0$^b$ |
| Individual weight (in kg, at 17 days) | 4.58$^a$ | 4.01$^b$ | 4.02 | 4.20 |

$^{a,b}$statistically significant intra-group differences (Anova III, $p < 0.05$)

Observations:

In group 1, significantly less neonatal diarrhea is observed in the test batch compared with the control batch. The same applies for the number of antibiotic treatments per box, over the 21 days of test and observation. The average weight of the piglets is +570 g higher for the piglets of the test batch compared with the control batch, this difference being statistically significant.

In group 2, despite an identical percentage of boxes affected by diarrhea between the test batch and the control batch, a reduction in the number of antibiotic treatments is noted in the test batch, and a drop in the mortality associated with digestive troubles, which are both statistically significant. This indicates that, even if the test or control animals of group 2 exhibited the same percentage of diarrhea, an advantage is identified in the animals that received the composition according to the invention (the diarrhea is less acute).

1. CONCLUSIONS

The results of this test make it possible to confirm the significance of application of the solution according to the invention to the teats and the perineum of sows, compared with absence of application. Thus, if internal (via ingestion from sucking the teats) and external (via contact with the mother's perineum) seeding of positive flora in the piglet is favored from the parturition, the health of these young animals is improved, and in particular the digestive health, which results in a significant reduction in the number of antibiotic treatments and/or neonatal diarrhea, and indeed digestive mortality.

1. Post-Test Observations

The breeder involved in this test wished to continue with the applications on the following 8 groups (groups 3 to 10).

The same protocol was followed, but only for the test rooms. The results are very satisfactory, and, according to the breeder, a significant reduction in neonatal diarrhea has been observed.

This continuance with the test caused the breeder to change their management of pathologies in young piglets, in particular by stopping the systematic antibiotic treatments, and limiting the use thereof to products such as drying agents.

The invention claimed is:

1. A method for prevention or treatment of infections contracted by a newborn livestock mammal at the time of birth, said method comprising a step of applying a composition to the perineum and/or to the teats of the female that is going to give birth or has given birth to said newborn livestock mammals, before and/or after parturition,
    wherein the composition comprises or consists essentially of a mixture of:
        three *Bacillus subtilis* strains: NOL01, NOL02, NOL03, said *Bacillus subtilis* strains being deposited in the CNCM under the numbers: CNCM I-4606, CNCM I-5043 and CNCM I-4607, respectively, and
        a lactic acid bacteria strain: *Lactococcus lactis* spp *lactis* 1 strain NOL11, said strain being deposited in the CNCM under number CNCM I-4609.

2. The method according to claim 1, wherein the composition comprises $10^4$ to $10^{11}$ bacterial colonies of said *Bacillus subtilis* strains and $10^4$ to $10^{11}$ bacterial colonies of said lactic bacteria strain, the bacterial colonies being per ml or g of composition.

3. The method according to claim 1, wherein said *Bacillus subtilis* strains are in sporulated and/or vegetative form.

4. The method according to claim 1, wherein said female is in an environment previously treated with the composition.

5. The method according to claim 1, wherein said infections are intestinal infections.

6. The method according to claim 1, wherein said infections are selected from the group consisting of neonatal diarrhea, enteritis, *salmonella*, rhinitis, pasteurellosis, bordetellose, ulcers, epidermitis, necroses, and infectious lameness.

7. The method according to claim 1, wherein said infections are intestinal infections, and wherein said composition is applied to the perineum and/or the teat(s) by spraying, spreading, powdering or soaking.

8. The method according to claim 1, wherein said infections are neonatal diarrhea.

9. The method according to claim 1, wherein said infections are ear necrosis, rhinitis and arthritis.

10. A kit for preventing digestive, respiratory or other infections in newborn livestock mammals, substantially comprising:
    at least a composition comprising or consisting essentially of a mixture of:

three *Bacillus subtilis* strains: NOL01, NOL02, NOL03, said *Bacillus subtilis* strains being deposited in the CNCM under the numbers: CNCM I-4606, CNCM I-5043 and CNCM I-4607, respectively, and a lactic acid bacteria strain: *Lactococcus lactis* spp *lactis* 1 strain NOL11, said strain being deposited in the CNCM under number CNCM I-4609, and at least one application means for applying said composition to the perineum and/or to the teats of the female that is going to give birth or has given birth to said newborn livestock mammals.

\* \* \* \* \*